United States Patent
Perler et al.

[11] Patent Number: 5,873,725
[45] Date of Patent: Feb. 23, 1999

[54] SUPPORT POST AND METHOD FOR CORONAL PROSTHESIS

[76] Inventors: Robert Perler, 43 Stony Run, New Rochelle, N.Y. 10804; William Wager, 905 Maple Creek Ct., Reno, Nev. 89511

[21] Appl. No.: 747,717

[22] Filed: Nov. 12, 1996

[51] Int. Cl.$^6$ .................................................. A61C 5/08
[52] U.S. Cl. ........................................ 433/221; 433/220
[58] Field of Search ................................ 433/220, 221

[56] References Cited

U.S. PATENT DOCUMENTS

| | | | |
|---|---|---|---|
| 1,589,994 | 6/1926 | Simmons | 433/221 |
| 3,524,255 | 8/1970 | Kurer | 433/221 |
| 4,952,150 | 8/1990 | Schiwiora et al. | 433/220 |
| 5,073,112 | 12/1991 | Weil | 433/221 |
| 5,104,321 | 4/1992 | Filhol | 433/221 |
| 5,181,850 | 1/1993 | Neumeyer | 433/221 |
| 5,277,583 | 1/1994 | Chalifoux | 433/220 |
| 5,284,442 | 2/1994 | Peterson | 433/223 |
| 5,326,264 | 7/1994 | Al Kasem | 433/220 |
| 5,348,476 | 9/1994 | Cohen et al. | 433/220 |
| 5,518,399 | 5/1996 | Sicurelli, Jr. et al. | 433/220 |
| 5,564,929 | 10/1996 | Alpert | 433/220 |

*Primary Examiner*—John J. Wilson
*Attorney, Agent, or Firm*—Handal & Morofsky

[57] ABSTRACT

The problems of stability and life of dental restoration disposed in root canals are addressed by a support post for a coronal prosthesis having a ceramic layer of hydroxyapatite, or equivalent, sputter-deposited or plasma sprayed on to a metal support post pretreated with an oxide, by abrasion or by etching.

26 Claims, 3 Drawing Sheets

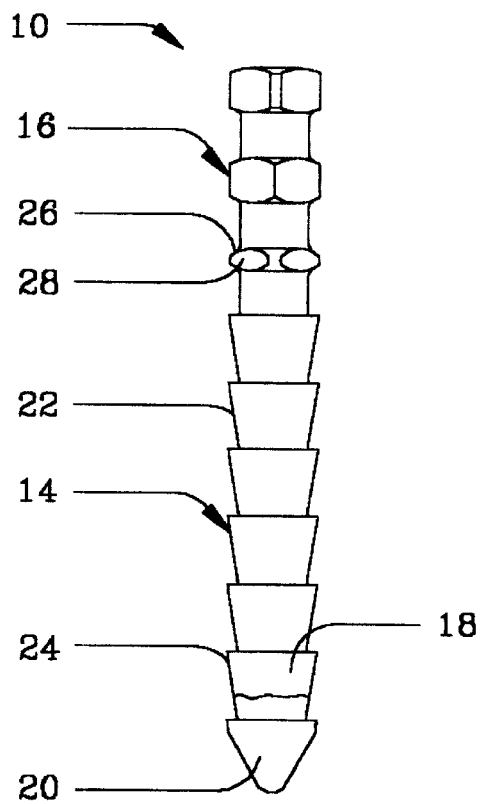
Figure 1
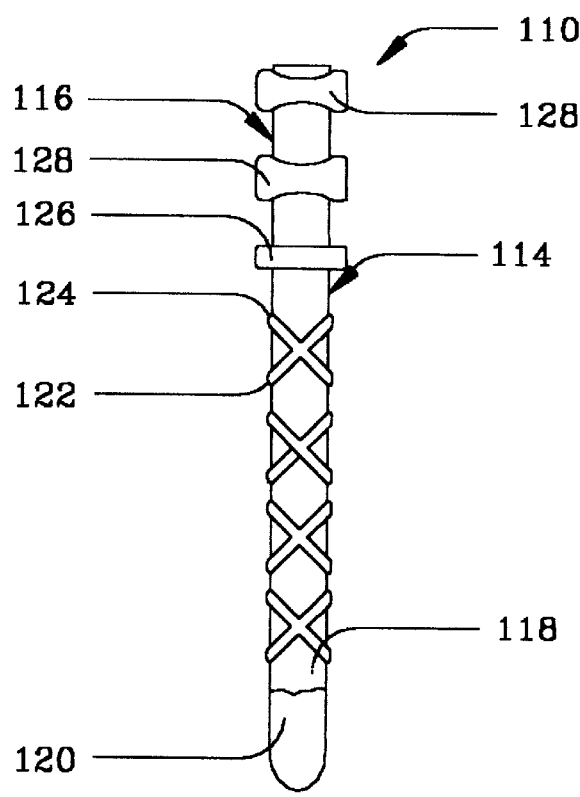
Figure 2
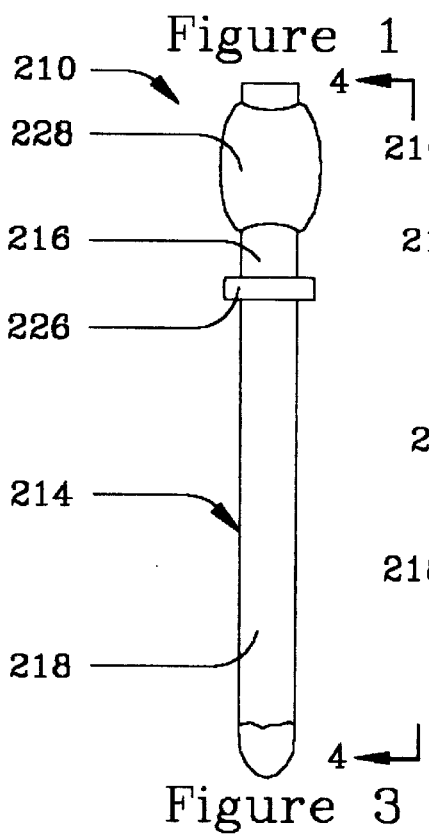
Figure 3
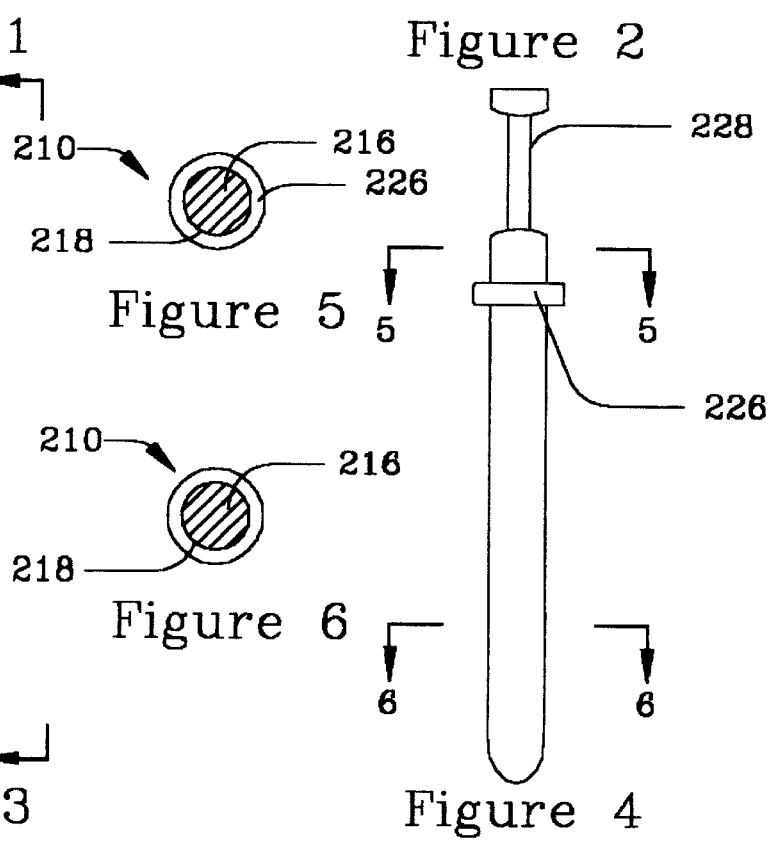
Figure 5
Figure 6
Figure 4

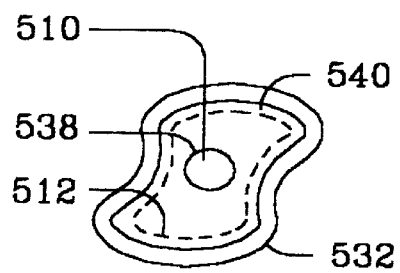
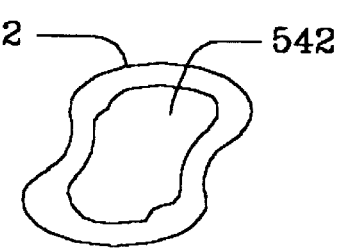
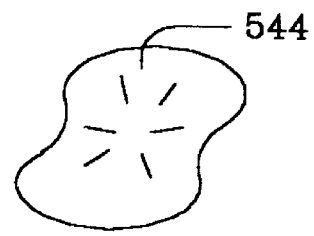
Figure 13     Figure 14     Figure 15
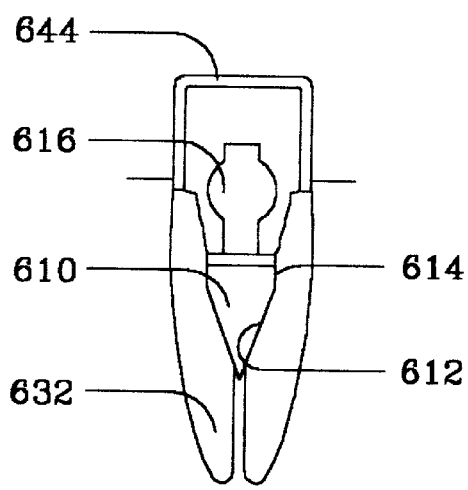
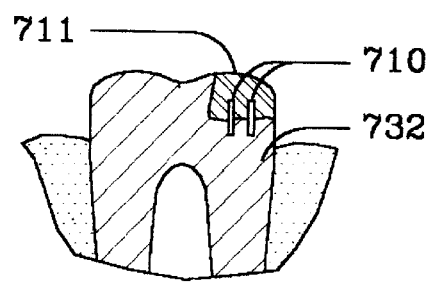
Figure 16     Figure 17

SUPPORT POST AND METHOD FOR CORONAL PROSTHESIS

TECHNICAL FIELD

The present invention relates to the field of restorative dental pins and posts adapted to support a crown and other dental restorations.

BACKGROUND

Ever since the advent of root canal therapy, a need has existed to reinforce and replace missing tooth structure. A tooth, after performance of root canal therapy, is more brittle than a live tooth. Most often its morphology is compromised and, given that its blood supply no longer exists, the tooth is more susceptible to fracture. Root canal therapy, is often required on account of pulpal trauma. Also, when a tooth has fractured horizontally to the point where remaining tooth structure can no longer support a restoration, root canal therapy becomes an important option to consider in providing more vertical support, albeit internal, for a restoration.

After root canal treatment the tooth is, in its remaining anatomy and structural support, analogous to a hollow tube in need of 1) internal support, and 2) a method of securing a coronal prosthesis. To put it another way, if you liken a post treatment tooth and the coronal prosthesis to a pair of hollow tubes, then the post would be the dowel that would be inserted through both tubes to hold them together.

From an engineering perspective, the length of post inside the tooth should exceed the length of the restoration to be placed on it. The fulcrum on the post created with lateral forces should exist within the tooth and the moment created with lateral forces should be less at the fulcrum point externally than internally. A post should enhance the mechanical properties of the tooth, and it should react to stresses similarly. It should allow the completely restored construct to function like a natural tooth, and ideally, be the same, or nearly the same, color.

Principal design criteria for clinically effective post and pin holes are prior art in the field of dentistry. Choosing the best canal, utilizing optimal tooth structure to maximize surface area, is also known to dentistry, and those schooled in the art of the restoration of candidate teeth.

Present day posts and pins fall into two categories: cast and prefabricated. The invention is primarily concerned with prefabricated posts, although it can be applied to cast posts. Indeed, cast posts have their own design criteria and sometimes they are the only posts that can be created when limiting factors exist. Such limiting factors include, but are not limited to, cross-sectional shape and diameter of root, and root curvature. Such cast posts may be treated using the subject concepts of the invention and used in the same way that the invention is applied to prefabricated posts.

Prefabricated posts come in all shapes and sizes, however, for the most part, they are made from metal materials such as stainless steel or other cobalt chrome alloys titanium, gold or brass.

As is well known in the art, the conventional support post is cemented in the hole in the tooth left after the performance of the root canal therapy. In most cases, the hole is substantially cylindrical in shape, this being the shape usually prepared in the root of the tooth after root canal therapy by a dentist's drill. In other cases, the hole is conical in shape, with the apex of the cone pointing toward the apes of the root of the tooth. This shaped hole can also be made by a drill or file. However, these conical holes, with various degrees of taper, are made by drills or files of conical shape which are selected to accommodate a tooth with limited root structure.

After root canal therapy, a hole is established in the root of the tooth. The hole is oversized with respect to the post by approximately 0.025 mm and a post with a base portion matching the shape and size of that hole is selected and cemented into the hole. After the post is cemented in the hole, a quantity of filled resin or amalgam is put over the top of the post in order to build up a core for the support of the coronal prosthesis. Such filled resin is selected for its strength properties in thick layers. Typically, such resin is of the dual cure variety, that is a resin which is prepared by mixing two plastic components together and curing them. In the case of a dual cure resin, curing or hardening will occur automatically after a period of time, or curing can be accelerated using a light source of appropriate wavelength (an auto-polymerizing or self-curing resin may also be used). Typically, such resins are filled with fibers or glass.

After the core resin has been deposited and hardened, it is then shaped to form the final core used to support the coronal prosthesis or crown. After shaping, an impression is taken of the finished core and the teeth proximate to it, and the same may be sent to a lab to allow the fabrication at the lab of a suitable coronal prosthesis.

When the coronal prosthesis has been made, it is returned to the dentist who checks to see that it properly matches the adjacent teeth and the core, and then cements it in place permanently. Typically, a two part cement, e.g. zinc oxyphosphate, polycarboxylic acid, glass ionomer, or bis -GMA- luting agent or other cement is used. This cement is of the time cured variety and hardens after a short period of time, securing the crown to the post. As a result of this multi-step process, the finished assembly of the natural root, post, core and crown forms a restored tooth and takes the place of the completely natural tooth. This restoration can be expected to function for many years.

When failure does occur, it typically takes the form of a failure in adhesion at the interfaces between the post and adjacent members of the restored tooth structure. One possibility is that the layer of cement between the base portion of the post and the root will usually fail due to microleakage of cement, causing the post, crown and core to become loose and fall out. Another possibility is that the filled resin dispensed around the top of the post will detach from the top of the post, causing the crown and core to become loose and fall out.

In an attempt to address these problems, numerous artifices have been developed to increase the adhesion between the base of the post and the root of the tooth. Thus, some posts are provided with threads which effectively increase their surface area at the post/root interface. Threads, grooves or other surface macrotexture also provide space for cement to be contained, which may be of particular importance in the case of a cylindrical post, where the space between the outside diameter of the post and the hole in the root may be minimal.

In similar fashion, cylindrical posts may also be provided with axial fluting on their outside surface. Some posts are also provided with threads or fluting. The objective of such surface structures is to increase the surface area of the post available for adhesion and reduce hydrostatic pressure within the cement and thus improve adhesion between the post and the root by providing more surface area for cement between the post and the root. Increasing the surface area of a post also increases the area over which stresses are distributed during chewing and other normal activities.

Because stresses are distributed over a larger area, the amount of stress per unit area during any activity is less and, thus, improves the longevity of the cement layer in the dental restoration. Vertical fluting may also be used to reduce hydrostatic pressure in the canal by allowing cement flow out of the top of the post and the bottom of the post.

In similar fashion, the top of the post to which the restoration shall be ultimately attached is often provided with increased surface area through various means in order to improve adhesion between the core and the post.

Notwithstanding the above measures, many restorations fail over time on account of a failure in the cement layer adjacent to the bottom of the post or a failure in adhesion at the top of the post. This occurs because the adhesion between the post and the cement at its bottom or the core material at the top of the post is primarily a mechanical adaptation of the cement to the post. Specifically, the hardened cement used at the bottom of the post forms a separate mechanical member which has adapted to crevices and forms around protuberances in the inside surface of the hole in the root of the tooth. Thus, adhesion between the root and the bottom of the hole can be viewed as the grip provided by interlocking mechanical members, namely, the root and the post bottom, and the layer of cement in between them.

With time, the hardened cement layer between the post and the root, starts to disintegrate, due to repeated mechanical shocks, resulting in loss of structural features which are critical to the maintenance of the interlocking structures that form the interfaces between the cement and the root canal, and between the cement and the post bottom. A breakdown in the integrity of the interlocking structures may result in microleakage at the cement/tooth interface. Microleakage may also be the cause of cement breakdown, which is then exacerbated by mechanical shocks.

While it is possible to improve the strength of the hardened cement by incorporating fiber, titanium alloy particles or other materials into it, such improvement in strength does little to change the retentions within the tooth. The conventional approach to the problem of cementing a post in a root canal has been to closely match the post to the canal in size and shape, and to have as thin a layer of cement as possible. Thus, the cement or luting agent used in this application is selected for its strength in thin layers.

In the fabrication of the core for the support of the coronal prosthesis, a filled epoxy having strength when deposited in thick layers is used. As previously noted, while a filled epoxy material is used for this particular part of a dental restoration, adhesion problems may still remain between the core and the top of the post.

SUMMARY OF THE INVENTION

In accordance with one embodiment of the invention, the above-described problems are addressed in a coronal prosthesis support post and adhesive structure which provides for stability and life of dental restorations disposed in root canals. The same is achieved through the use of a multi-layer adhesive structure comprising a layer of oxide chemically or molecularly bonded to a metal support post and a layer of ceramic material sputter-deposited or plasma sprayed over the oxide in a manner which also results in molecular bonding between the oxide and the ceramic.

In accordance with a particularly preferred embodiment of the invention, a stainless steel, chrome cobalt alloy, titanium, or other suitable post is roughened through the use of a surface "sandblasting" step, or alternatively, chemical etching or other procedure calculated to roughen the external surface of the post in a very shallow fashion, thereby allowing the use of a thin layer to be adhered to the post, and depositing a layer of ceramic hydroxyapatite ($Ca_5(PO_4)_3OH$) or similar ceramic, over the thus roughened surface without the use of a layer of oxide. Because of the chemical composition of the apatite, it has the characteristic of achieving a bond with some degree of chemical character with the luting agent cement materials typically used in dentistry. Likewise, these cements exhibit chemical bonding to the natural tooth structure. Finally, the subject apatite or other suitable ceramic coating may demonstrate enhanced adhesion by chemically bonding to the epoxy used to build up the core for the support of the coronal prosthesis.

BRIEF DESCRIPTION OF THE DRAWINGS

Several illustrative ways of practicing the invention are described herein with particular reference to the drawings, in which:

FIG. 1 is a plan view of a dental post constructed in accordance with the present invention;

FIG. 2 is a plan view of an alternative embodiment of the present invention;

FIG. 3 is a plan view of an embodiment of the invention having a pair of flat surfaces;

FIG. 4 is a view along lines 4—4 of FIG. 3;

FIG. 5 is a view in cross section along lines 5—5 of FIG. 4 illustrating the dental post illustrated in FIG. 3;

FIG. 6 is a view along lines 6—6 of FIG. 4 illustrating a surface coating in accordance with the present invention;

FIGS. 10–15 illustrate successive steps in the restoration of a tooth in accordance with the teachings of the present invention;

FIG. 16 is a cross-sectional view of a restoration in accordance with the present invention; and FIG. 17 is a cross-sectional representation of a tooth incorporating a dental pin fabricated in accordance with the present invention.

DETAILED DESCRIPTION OF THE PREFERRED EMBODIMENT

Figure 7:
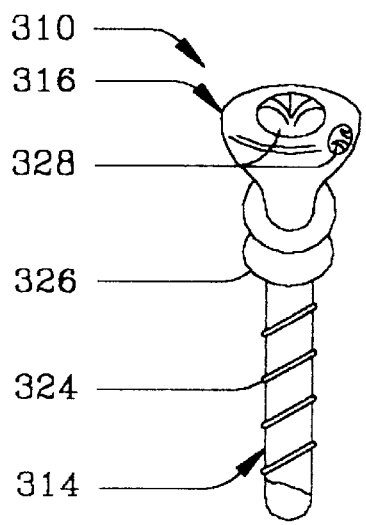
FIG. 7 is a perspective view of yet another alternative embodiment of the dental post of the present invention.

In accordance with the preferred embodiment of the invention, a post and pin of relatively conventional configuration is used as the starting point for the manufacturing process. The description is largely written in terms of post fabrication and use and it is understood that coated pins of conventional configuration may be used in conventionally configured pinned restorations. Such posts are well known and come in a variety of configurations. In accordance with the preferred embodiment of the invention, a wide variety of known configuration posts of various designs and geometries may be used. Metal is the preferred post material, and the invention may be practiced using posts made of titanium, titanium alloy, stainless steel, chrome cobalt alloy, gold, brass, or any other suitable metal. Alternatively, a composite such as a reinforced polymer may be used.

Therefore, in accordance with the invention, acceptable configurations for the prefabricated dental posts of the present invention include posts with squared, annularly articulated post tops, post tops incorporating passages for the incorporation of core material into the center of the post top, multi-annular ridge tops, dental posts with spiral ridges on their lower portions, posts with angular ridges on their lower portions, threaded and fluted posts, posts with two spiral ridges oriented in opposite senses on their base, as well as posts with substantially smooth surfaces, and any combination of the above.

As noted above, the first step in the manufacture of a typical post constructed in accordance with the present invention is the manufacture of a metal dental post, or a titanium plasma sprayed dental post or a dental post of other suitable material capable of receiving the deposit of hydroxyapatite (HA) or other ceramic material. Other coatings are also possible, such as plastic, e.g. acrylic polymer or acrylic co-polymer but hydroxyapatite is preferred for its rigidity, long life and chemical affinity. Such posts may be manufactured in a wide range of sizes. For example, in the case of a post meant for use in humans, lengths in the range of 8 to 15 millimeters are common. For specialized applications, posts with lengths, in the range of 2 through 22 millimeters are commercially available. Such sizes are also suitable for application of the teachings of the present invention.

The invention is also applicable to a wide range of post diameters and may also be applied to using convention al post diameters which are typically in the range of 0.1 through 2.1 millimeters.

The next step in the fabrication of the inventive dental post is the application of an thin layer of hydroxyapatite or other suitable ceramic materials. In accordance with the invention, it is necessary that a strong bond be formed between the dental post and the layer of hydroxyapatite. The same is insured by first putting the substrate post through a cleaning regimen not unlike that used to clean metals before the deposition of hydroxyapatite in, for example, the manufacture of a dental implant. Generally, the techniques for the deposition of the ceramic hydroxyapatite to metallic posts are the same as the techniques employed in the manufacture of metallic dental implants. These techniques are well known in the art and form no part of the invention except as may be specifically detailed herein. Alternatively, other coating methods, demonstrated to result in a strong coating-substrate bond, may be employed.

After the cleaning steps have been performed and the cleaning regimen completed, the next step is to increase the surface area of the metal post by roughening it. Acceptable means for roughening the surface of the post is "sandblasting" it with a material capable of introducing fine scratches or microtextures into the surface of the post. In accordance with the preferred embodiment, a stream of gas with particles of alumina ("$Al_2O_3$" herein) entrained in it is directed upon the surface of the post to be roughened and the surface is "sandblasted" until the surface is substantially covered with scratches or microtextures, with the scratches or microtextures being separated by distances on the order of the width of a scratch.

A jet of clean air, ultrasonic cleaning, or other suitable means, is then used to substantially remove any residual particles of $Al_2O_3$. Alternatively, or in addition, a jet of water may be used. After the application of the water, the post may be dried with a jet of hot air, which also serves to mechanically blow away and evaporate any remaining water particles.

As an alternative to preparing the surface by roughening it with a jet of air with entrained particles, or other mechanical technique, it is possible in accordance with the present invention to achieve the desired roughening by means of chemical etching of the surface.

After the surface has been roughened, it is ready to receive a layer of hydroxyapatite or other suitable ceramic. In accordance with the invention, the hydroxyapatite is applied using a plasma spray or sputter deposition technique. In accordance with plasma spray deposition techniques, which are well known in, for example, the field of hydroxyapatite deposition on dental implants, a jet of a gas or gases is delivered to an arc, creating a plasma. The stream of hydroxyapatite particles is then introduced into the plasma which may be applied in a chamber or in the ambient air. Generally, deposition is done by placing the posts or pins in front of the plasma flame produced by the ionized gases. The temperature in the arc is on the order of 10,000 to 30,000 degrees centigrade. As a result, ceramic materials in the jet of gas delivered to the arc are melted, and are deposited on the surface of the target, in this case, the post.

As the hydroxyapatite is delivered to and melted by the arc that forms the plasma, the roughened post to be coated with hydroxyapatite is passed in front of the plasma spray and a thin layer of hydroxyapatite is deposited on it. Typically, the amount of hydroxyapatite deposited in a single pass through the plasma is not enough to substantially cover the surface and several passes in front of the plasma spray are employed to get the desired substantially complete coverage. The actual thickness of the hydroxyapatite may be in the range of 25 to 40 microns but is exaggerated in the Figures for purpose of clarity of illustration. As successive layers are applied, each new layer of the hydroxyapatite will tend to mature, or improve the strength and crystallinity of the previous layer or layers of hydroxyapatite, although those of ordinary skill in the art are able to get a sufficiently strong and cured layer in a single pass through the arc by selecting the various parameters of the system.

In accordance with the invention, as alluded to above, the object is to have a thin layer of the hydroxyapatite extending around the metal post forming a well adhered band which helps to maintain its own integrity, while at the same time securely mating with and fitting into the roughened surface of the metal dental post.

As illustrated in FIG. 1, a dental post 10 constructed in accordance with the present invention, comprises a base 14 which is a relatively long stem-like member. The upper portion of post 10 comprises a top 16 with a shape designed to securely lock into the material securing the top 16 to and supporting the crown.

The inventive post 10 has a thin coating of hydroxyapatite 18 all over its surface area, except for its tip 20. Tip 20 is left bare only because this is the region by which the inventive post 10 is held by a gripping device during the plasma deposition of the hydroxyapatite, and the gripping device blocks the deposition of hydroxyapatite on that portion of the inventive post. The post may be entirely coated, however. Also, when posts are cut to length, this area is adjacent to the cut which is left without any coating. As is illustrated in FIG. 1, the base 14 of the inventive dental post 10 includes surface features 22 configured to promote a mechanical adaptation between the inventive post 10 and the luting agent or cement placed in the root canal as a result of the performance of root canal therapy. Appropriate cements may be of the chemically or mechanically bonding type. Preferably the cement is a resin adhesive cement. Appropriate cements and luting agents include glass ionomers, autopolymerizing resins, photo polymerizing resins, zinc phosphate, zinc polycarboxylate, zinc oxide-eugenol with and without 2-ethoxybenzoic acid (EBA), silicophosphate cement, organophosphates, hydroxyethyl methacrylate (HEMA), and 4 methacrylethyl trimellitic anhydride (4-META). In accordance with the preferred embodiment, HEMA and 4-META cements are preferred. Resin luting agents should be selected to ensure maximum polymerization of the resin in the less accessible proximal areas.

In the case of the post illustrated in FIG. 1, surface features 22 take the form of frustro conical annular ridges 24. Likewise, the top 16 of the inventive dental post 10 comprises surfaces configured and dimensioned to support the crown and provide a stable mechanical structure. In particular, top 16 includes a faceted flange 26 which has a number of facets 28.

An alternative post 110, constructed in accordance with the present invention is illustrated in FIG. 2. It includes a base 114, and a top 116. Post 110 is coated with a layer of hydroxyapatite 118, except for its bare tip 120. Mechanical engagement is provided by a pair of oppositely oriented helical threads 122 and 124. A flange 126 provides the usual support against the top of the canal within which the post is supported in the finished dental restoration. Proper mechanical support for the crown in the finished restoration is provided by a pair of flat surfaces 128 stamped in the top 116 of the post 110.

In the case of the present invention, because of the exceptional strength of the bonds achieved between the hydroxyapatite, the bonding mechanism, and the dentin of the tooth, the use of a post with a smooth surface without protruding structural surface features is preferred in the case of many restorations. Such a post is illustrated in FIGS. 3–6. In this embodiment, the inventive post 210 includes a base 214 and a top 216. It is coated with a layer of hydroxyapatite 218 and includes a flange 226. Support for the crown and adhesion is provided by a stamped flat face 228, as is illustrated most clearly in FIG. 4.

Still another post 310 constructed in accordance with the present invention is illustrated in FIG. 7. Post 310 which may be hollow and pipe like includes a base 314, a top 316, a single helical thread 344, a flange 326 and a number of holes 328 which pass through the top 360 of post 310 and communicate with each other to allow the cement to enter the holes and join with itself to provide a chain-like member supporting the crown, while simultaneously reducing hydrostatic pressure.

Figure 8:
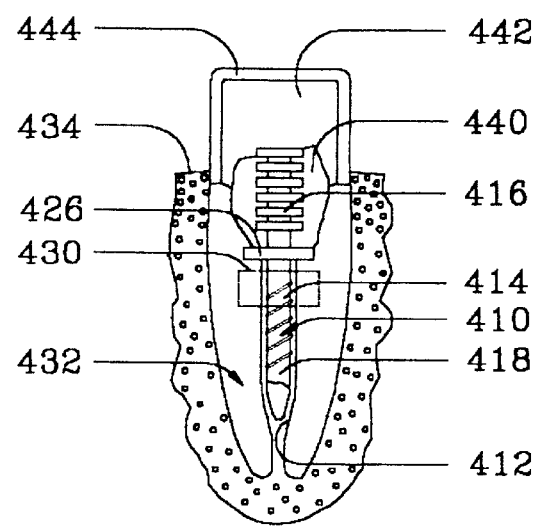
FIG. 8 is a cross-sectional view of a dental restoration in vivo.
Figure 9:
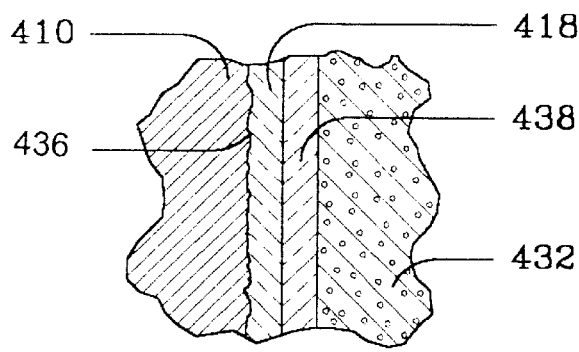
FIG. 9 is a cross-sectional view illustrating surface interfaces in a restoration made in accordance with the present invention.

A finished restoration completed in accordance with the present invention is illustrated in FIG. 8. The restoration comprises a post 410 disposed in the root canal 412. The base 414 of post 410 is disposed in root canal 412. A coating of hydroxyapatite 418 is deposited over the middle of post 410 and is thus in facing spaced relationship to canal 412. The inventive post 410 is comprised of a top 416 which is also coated with hydroxyapatite in accordance with the process described above, namely, plasma deposition, although alternative coating procedures for deposition of hydroxyapatite or other suitable ceramic materials may be employed. Finally, axial stability is maintained with a flange 426. As can be seen in FIG. 8, the dentin 430 of tooth 432 is supported within the periodontal apparatus 434 of the patient. As can be seen most easily with reference to FIG. 9, the metal of post 410 has a roughened surface 436 on account of its being acid etched, or "sandblasted". Accordingly the layer of hydroxyapatite 418 is securely locked onto the middle of post 410. Likewise, because of the chemical affinity between the hydroxyapatite 418 and the cement 438, a strong chemical bond is formed at the interface of the hydroxyapatite 418 and the cement 438.

Referring back to FIG. 8, the restoration is completed by a resin core 440 made of resin which together with an additional quantity of cement 442, which extends below the gum line, supports and secures crown 444. Core 440 adheres to the apatite coating 418, which, in turn, is secured to the metal of post 410 on account of the roughened surface of the top 416 of post 410.

Figure 10:
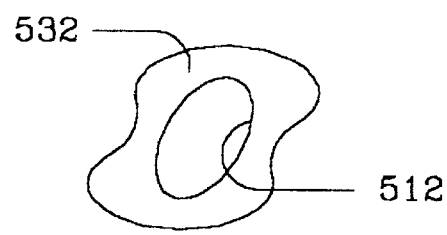

Referring to FIG. 10, a post of appropriate size is selected for insertion into the root canal 512 of a treated tooth 532. The canal 512 has its post space apical extent defined using a relatively thin preshaping drill. The shaping of the canal 512 is then completed with a thicker finishing drill.

Figure 11:
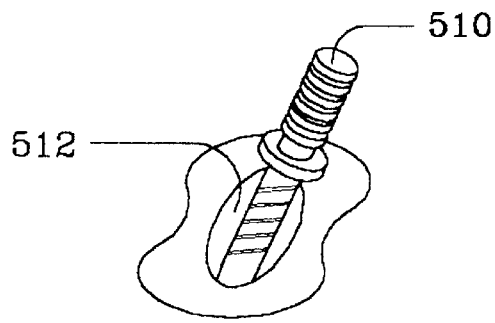

As shown in FIG. 11, a post 510 is then placed into the canal 512, in order to test the size of the canal. At the same time, the dentist notes the depth to which the post is inserted into the canal, and if the canal is properly configured and dimensioned, notes the length of the post and determines where it is to be cut.

Figure 12:
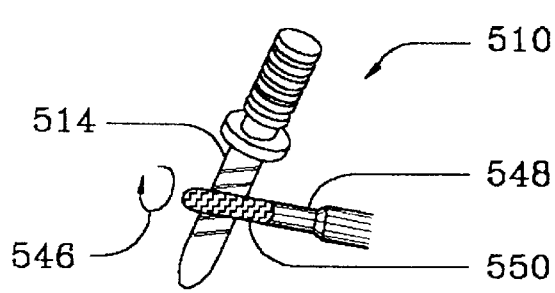

Such cutting may be accomplished using any number of means. For example, a rotary diamond bur rotating in the direction of arrow 546 will function appropriately to cut the base 514 of post 510, as illustrated in FIG. 12. As is apparent, the diamond bur bit 548 includes a tip with diamond chips 550 which when rotated is an effective abrasion and cutting device.

One then fills the canal with a quantity of cement 538. The post 510 is then inserted into the adhesive-lined canal 512, in tooth 532 as illustrated in FIG. 13. After post 510 is cemented in the hole, an additional quantity 540 of resin is put over the top of the post in order to build up a core, typically with a filled resin as illustrated in FIG. 14 for the support of the coronal prosthesis. Such filled resin, or alloy is selected for its strength properties in thick layers. Such resin is usually of the dual cure variety, that is a resin prepared by mixing two plastic components together and curing them. In the case of a dual cure resin, curing or hardening will occur automatically after a period of time, or curing can be accelerated using a light source in the appropriate frequency range.

After the core resin has been deposited and hardened, it is then shaped as illustrated in FIG. 14 to form the final core 542 used to support the coronal prosthesis or crown. After shaping, an impression is taken of the final core and. the teeth proximate to it, and the same can be sent to a laboratory to allow the fabrication at the lab of a suitable coronal prosthesis 544.

Once the coronal prosthesis 544 has been made, it is received by the dentist who checks to see that it properly matches the adjacent teeth and the core 542. It is then cemented in place. The crown 544 may then be applied to complete the restoration, as illustrated in FIG. 15. The cement is then allowed to cure.

Typically, a two part cement is used for final prosthesis attachment. This cement is of the time cured variety and hardens after a short period of time, securing the crown to the post and prepared tooth. After this, the finished assembly of the natural root, post, core and crown forms a restored tooth and takes the place of the completely natural tooth. This restoration can be expected to function for many years.

As noted above, the bond between the cement and the post 510 is extremely strong because of the natural strength of the bond between the two part cement and hydroxyapatite or other suitable ceramic coating.

In above illustrated case, the hole is substantially cylindrical in shape, this being the shape usually left behind in the root of the tooth after root canal therapy using a dentist's drill.

In accordance with the present invention it is also possible to fabricate a reinforced polymer post such as a carbon fiber post and coat the same with an acrylic material.

As noted above, the canal 612, as illustrated in FIG. 16 may also be conical in shape, ending in or defining a point which is pointing toward the apex of the root of the tooth 632. This shape hole is also made by a drill or other suitable instrumentation. These conical cavities, with various degrees of taper, are made by drills of conical shape which are selected to accommodate a tooth which has reduced tooth structure, and accommodate a post, such as post 610 in FIG. 16.

Post 610 has a conical base 614 and a top 616 of conventional configuration to provide a support for a conventional crown 644.

Referring to FIG. 17, a pair of pins 710 made of stainless steel and coated with hydroxyapatite in accordance with the present invention are used to maintain the structural integrity of a filling 711 in a tooth 732.

While illustrative embodiments of the inventions have been disclosed, modifications of the same will be obvious to those of ordinary skill in the art. Such modifications are within the spirit and scope of the invention which is limited and defined only by the following claims:

We claim:

1. An elongated coronal prosthesis support post made of metal comprising a base portion with an outside surface and a non-metallic layer of ceramic material deposited over and bonded to said outside surface to facilitate adhesion of the support post to a dental adhesive, said non-metallic layer presenting an external surface having a ceramic character for bonding to said dental adhesive, and wherein said ceramic material layer and said external surface consist essentially dentally compatible apatite material.

2. A coronal prosthesis support post according to claim 1, wherein said outside surface of said post is roughened to an extent sufficient to substantially increase the strength of the bond between said post and said ceramic material.

3. A control prosthesis support post according to claim 2, wherein said roughening is of the type and magnitude provided by abrading using abrasive particles entrained in a gaseous stream or by chemical etching.

4. A coronal prosthesis support post according to claim 2, wherein said metal is selected from the group consisting of stainless steel, titanium, titanium alloy, stainless steel, gold, and brass.

5. A coronal prosthesis support post according to claims 2, wherein said ceramic layer material consists essentially of hydroxyapatite.

6. A coronal prosthesis support post according to claimed 1, wherein said ceramic layer consists essentially of hydroxyapatite.

7. A coronal prosthesis support post according to claim 1, wherein said post has a post lenght between 2 mm and 22 mm.

8. A coronal prosthesis support post according to claims 7, wherein said post has a diameter between 0.1 mm and 2.1 mm.

9. A coronal prosthesis support post according to claim 1, wherein said support post comprises:
top portion having a top surface configured and dimensioned to support a coronal prosthesis.

10. A coronal prosthesis support post according to claim 9, wherein said base of the support post has a surface configured with frusto-conical annular ridges to promote mechanical coupling between the support post and the root canal.

11. A coronal prosthesis support post according to claim 9, wherein said top comprises a faceted flange having a number of facets.

12. A coronal prosthesis support post according to claim 1, wherein said base portion is essentially smoothly shaped, and the support post comprises a top portion configured and dimensioned to support a coronal prosthesis.

13. A coronal prosthesis support post according to claim 12, wherein said base has a surface defining a pair of oppositely oriented helical threads.

14. A coronal prosthesis support post according to claim 12, wherein support for the coronal prosthesis is provided by a pair of flat surfaces stamped in said top of said post and a faceted flange having a number of facets.

15. A coronal prosthesis support post according to claim 12, wherein said base has a surface configured and dimensioned to resist rotation or removal.

16. A coronal prosthesis support post according to claim 1, comprising a top portion configured and dimensioned to support a coronal prothesis said top portion having a configuration of a squared post top, an annually articulated post top, a structure incorporating passages for the incorporation of core material, or a structure having a multi-annular ridged top, a spiral-ridged lower portion, an annularly ridged lower portion, or double spiral ridges oriented in opposites senses.

17. A coronal prosthesis support post according to claim 1, wherein the support post comprises a top portion configured and dimensioned to support a coronal prosthesis and wherein said top portion is coated with a dentally compatible apatite material for bonding with the dental adhesive.

18. A coronal prosthesis support post according to claim 1, comprising a layer of oxide chemically or molecularly bonded to the metal support post, said ceramic layer of apatite material being bonded to said layer of oxide.

19. A coronal prosthesis support post according to claim 1, comprising a top portion configured to support a coronal prosthesis and a metallic base portion configured to be adhesively secured in a root canal, said metallic base portion being coated, or essentially coated, except for a small uncoated portion, with a substantially rigid layer consisting essentially of hydroxyapatite to facilitate adhesion of the support post to a dental adhesive in the root canal.

20. A support post according to claim 19 wherein said base portion has a smooth shape without protruding structural surface features.

21. A support post according to claim 19 wherein said top portion is coated with dentally compatible apatite material to facilitate adhesion of the coronal prosthesis.

22. A method for restoration of a tooth after treatment by way of root canal therapy, comprising the steps of:

(a) providing an elongated coronal prosthesis support as claimed in claims 1 post of appropriate size for insertion into the root canal of a treated tooth, said post having, in addition to said base portion, a top portion, said ceramic material being sputter deposited on said post;

(b) defining the post space apical extent of the canal using a drill;

(c) ascertaining the depth of the canal;

(d) cutting said post to the appropriate size, if required;

(e) filling the canal with a quantity of adhesive sufficient to adhere the post to the canal;

(f) inserting the base portion of the post into the canal so as to expose said ceramic material to said adhesive to effect adhesion to the ceramic material;

(g) applying and curing a required quantity of cementing agent over the top of the post in order to build up a core;

(h) shaping the core to form a final core used to support the coronal prosthesis;

(i) taking an impression of the final core and the teeth near to said treated tooth; and (j) mounting a suitable coronal prosthesis on the top portion of the post and securing said prosthesis to said core.

23. A method for restoration according to claim 22, wherein said adhesive is selected from the group consisting of chemical-cure resins, light-cure resins, and dual-cure resins.

24. A method for manufacturing a coated dental post comprising the steps of:

(a) fabricating a metal dental post with a length of from about 2 to about 22 millimeters and a diameter of from about 0.1 to about 2.1 millimeters;

(b) cleaning said dental post to receive a deposit of a non-metallic ceramic material;

(c) roughening said post to increase the surface area of said post; and (d) sputter or plasma spray depositing, a thin non-metallic layer of a ceramic material on to the metal post intimately secured to the roughened surface of the post.

25. A method for manufacturing a dental post according to claim 24, wherein said ceramic material is hydroxyapatite.

26. A method for manufacturing a dental post according to claim 25, comprising roughening said post by treating the post with an abrasive material capable of introducing fine scratches or microtextures into the surface of said post, said gaseous material being entrained in a stream of gas.

* * * * *